US006165502A

United States Patent [19]
Oleske et al.

[11] Patent Number: 6,165,502
[45] Date of Patent: *Dec. 26, 2000

[54] PROTEIN-LIPID VESICLES AND AUTOGENOUS VACCINE COMPRISING THE SAME

[75] Inventors: James M. Oleske, Morris Plains; Thomas N. Denny, Cranford; Anthony J. Scolpino, Ramsey; Eleonora Feketeova, Harrison; Susan Gould-Fogerite; Raphael J. Mannino, both of Annandale, all of N.J.

[73] Assignees: Albany Medical College, Albany, N.Y.; Medical College of New Jersey, Newark, N.J.

[*] Notice: This patent is subject to a terminal disclaimer.

[21] Appl. No.: 09/188,120

[22] Filed: Nov. 9, 1998

Related U.S. Application Data

[63] Continuation of application No. 08/712,020, Sep. 11, 1996, Pat. No. 5,834,015.

[51] Int. Cl.$^7$ ...................................................... A61K 9/127
[52] U.S. Cl. .................. 424/450; 424/184.1; 424/188.1; 424/278.1; 424/812; 436/829
[58] Field of Search ................................. 424/450, 184.1, 424/188.1, 278.1, 812; 436/829

[56] References Cited

U.S. PATENT DOCUMENTS

| | | |
|---|---|---|
| 4,509,698 | 4/1985 | Anderson . |
| 5,026,557 | 6/1991 | Estis . |
| 5,834,015 | 11/1998 | Oleske . |

OTHER PUBLICATIONS

Chapter 15, *Lipid Matrix–Based Vaccines for Mucosal and Systemic Immunization,* Raphael J. Mannino and Susan Guold–Fogerite, pp. 363–387, P.D. 1995.

J. Oleske et al, Autogenous Vaccine in the Treatment of Laryngeal Papilloma, *Current Chemotherapy & Immunotherapy,* Proc. 12th Intl. Cong. of Chemotherapy, Florence, Italy Jul. 19–24, 1981, pp. 1099–1101.

J. Oleske et al, Juvenile Papilloma of the Larynx, *American Journal of Diseases of Children,* vol. 121, May 1971, pp. 417–419.

Charlotte R. Kensil et al, Structure/Function Relationship in Adjuvants from Quillaja saponaria Molina, *Vaccines 92.* Cold Spring Harbor Laboratory Press, 1992, pp. 35–40.

Charlotte R. Kensil, et al, The Use of Stimulon Adjuvant to Boost Vaccine Response, *Vaccine Research,* vol. 2, No. 4, 1993, pp. 273–281.

Mark J. Newman et al, Immunogenicity and Toxicity Testing of an Experimental HIV–1 Vaccine in Nonhuman Primates, *AIDS Research and Human Retroviruses,* vol. 8, No. 8, 1992, pp. 1413–1418.

Jia–Yan Wu et al, Accessory Cell Requirements for Saponin Adjuvant–Induced Class I MHC Antigen–Restricted Cytotoxic T–Lymphocytes, *Cellular Immunology,* vol. 154, pp. 393–406 (1994).

Jia–Yan Wu et al, Saponin Adjuvant Enhancement of Antigen–Specific Immune Responses to an Experimental HIV–1 Vaccine, *The Journal of Immunology,* vol. 148, pp. 1519–1525, No. 5, Mar. 1, 1992.

Mark J. Newman et al, Saponin Adjuvant Induction of Ovalbumin–Specific $CD8^+$ Cytotoxic T Lymphocyte Responses, *The Journal of Immunology,* vol. 148, pp. 2357–2362, No. 8, Apr. 15, 1992.

Charlotte R. Kensil et al, Separation and Characterization of Saponins with Adjuvant Activity from Quillaja saponaria Molina Cortex, *The Journal of Immunology,* vol. 146, pp. 431–437, No. 2, Jan. 15, 1991.

Jonas E. Salk, M.D. with Mary Contakos et al, Use of Adjuvants in Studies on Influenza Immunization, *J.A.M.A.,* vol. 151, No. 14, pp. 1169–1175, Apr. 4, 1953.

Barney S. Graham et al, Augmentation of Human Immunodeficiency Virus Type 1 Neutralizing Antibody by Printing with gp160 Recombinant Vaccinia and Boosting with rgp160 in Vaccinia–Naive Adults, *The Journal of Infectious Diseases,* 1993, vol. 167, pp. 533–537.

E. Celis et al, Regulation of the Human Immune Response to HBsAg: Effects of Antibodies and Antigen Conformation in the Stimulation of Helper T Cells by HBsAg, *Hepatology,* vol. 5, No. 5, 744–751, 1985.

Jonas Salk, Prospects for the Control of AIDS by Immunizing Seropositive Individuals, *Nature,* vol. 327, Jun. 1987, pp. 473–476.

Emil Bisaccia et al, Extracorporeal Photopheresis in the Treatment of AIDS–Related Complex: A Pilot Study, *Annals of Internal Medicine,* vol. 113, No. 4, Aug. 15, 1990, pp. 270–275.

Antonio Lanzavecchia et al, T Cells Can Present Antigens Such As HIV gp120 Targeted to Their Own Surface Molecules, *Nature,* vol. 334, No. 11, Aug. 11, 1988, pp. 530–534.

J.S. McDougal et al, Antibody Response to Human Immunodeficiency Virus in Homosexual Men, *The Journal of Clinical Investigation, Inc.,* vol. 80, Aug. 1987, pp. 316–324.

Robert B. Belshe et al, Safety and Immunogenicity of a Fully Glycosylated Recombinant gp160 Human Immunodeficiency Virus Type 1 Vaccine in Subjects at Low Risk of Infection, *The Journal of Infectious Diseases,* vol. 168, pp. 1387–1395, 1993.

(List continued on next page.)

*Primary Examiner*—Gollamudi S. Kishore
*Attorney, Agent, or Firm*—Sughrue, Mion, Zinn, Macpeak & Seas, PLLC

[57] ABSTRACT

A protein-lipid vesicle that can be used to make an autogenous vaccine comprises patient-specific antigen, adjuvant or immunomodulator, and lipid carrier. In addition, a negatively charged lipid component is desirably included. The autogenous vaccine is useful to treat individuals with chronic diseases, including chronic infectious diseases and neoplasias. The chronic infectious diseases that can be treated include disease caused by infection with human immunodeficiency viruses.

39 Claims, No Drawings

OTHER PUBLICATIONS

Bruce D. Walker et al, HIV–specific Cytotoxic T Lymphocytes in Seropositive Individuals, *Nature,* vol. 328, Jul. 23, 1987, pp. 345–348.

Patricia E. Stanhope et al, Human CD4+ Cytolytic T Lymphocyte Responses to a Human Immunodeficiency Virus Type 1 gp160 Subunit Vaccine, *The Journal of Infectious Diseases,* vol. 168, pp. 92–100, Jul. 1993.

Alberto Beretta et al, HIV env Glycoprotein Shares a Cross–Reacting Epitope With a Surface Protein Present on Activated Human Monocytes and Involved in Antigen Presentation, *Eur. J. Immunol.,* vol. 17 pp. 1793–1798, 1987.

Hana Golding et al, Common Epitope in Human Immunodeficiency Virus (HIV) I–GP41 and HLA Class II Elicits Immunosuppressive Autoantibodies Capable of Contributing to Immune Dysfunction in HIV I–infected Individuals, *The Journal of Clinical Investigation, Inc.,* vol. 83, pp. 1430–1435, Apr. 1989.

Claudo De Santis et al, Cross–Reactive Respsonse to Human Immunodeficiency Virus Type 1 (HIV–1) gp120 and HLA Class I Heavy Chains Induced by Receipt of HIV–1–Derived Envelope Vaccines, *The Journal of Infectious Diseases,* vol. 168, pp. 1396–1403, 1993.

David C. Redfield et al, Psoralen Inactivation of Influenza and Herpes Simplex Viruses and of Virus–Infected Cells, *Infection and Immunity,* vol. 32, pp. 1216–1226, Jun. 1981.

Philip O. Livingston, Approaches to Augmenting the IgG Antibody Response to Melanoma Ganglioside Vaccines, *Annals New York Academy of Sciences,* pp. 204–213.

David Gold et al, Viagene Begins New Gene Therapy Trial, *Treatment Issues,* vol. 8, No. 4, pp. 5–13.

Timothy L. Darrow, Ph.D., et al Immunotherapy of Human Melanoma with Gene–Modified Tumor Cell Vaccines *Cancel Control,* pp. 415–428, Sep./Oct. 1995.

Simon Wain–Hobson, Virological Mayhem, *News and Views.*

Gail Goodman–Snitkoff et al, Role of Intrastructural/Intermolecular Help in Immunization with Peptide–Phospholipid Complexes, *The Journal of Immunology,* vol. 147, pp. 410–415, Jul. 15, 1991.

M.G. Bernengo et al, The In Vitro Effect of a Calf Thymus Extract on the Peripheral Blood Lymphocytes of Patients with Warts, *British Journal of Dermatology,* vol. 102, pp. 11–16, 1980.

Snorri Ingimarsson et al, Side Effects of Long–Term Treatment with Human Leukocyte Interferon *The Journal of Infectious Diseases,* vol. 140, No. 4, pp. 560–563, Oct. 1979.

G. M. Scott et al, Effect of Injections of Small Doses of Human Fibroblast Interferon Into Genital Warts, *British Journal of Venereal Diseases,* vol. 55, pp. 442–445, 1979.

Sean Soltysik et al, Adjuvant Activity of QS–21 Isomers, *Annals of the New York Academy of Sciences,* vol. 690, pp. 392–395, Aug. 12, 1993.

A.C. White et al, A Purified Saponin Acts As An Adjuvant For a T–Independent Antigen, *Immunobiology of Proteins and Peptides VI,* pp. 207–210, 1991.

Charlotte R. Kensil et al, Novel Adjuvants from Quillaja saponaria Molina, *AIDS Research Review,* vol. 3, pp. 379–389, 1993.

P.B. Sehgal et al, Regulation of the Acute Phase and Immune Responses in Viral Disease. Enhanced Expression of the Beta 2–Interferon/Hepatoxyte–Stimulating Factor/Interleukin 6 Gene in Virus–Infected Human Fibroblasts, *J. Exp Med.* vol. 167; pp. 1951–1956 (1988).

R.D. Garman et al, Characterization of Helper Factors Distinct from Interleukin 2 Necessary for the Generation of Allospecific Cytolytic T Lymphocytes, *J. Immunol,* vol. 130; pp. 756–762 (1983).

N.J. Roberts, Different Effects of Influenza Virus, Respiratory Syncytial Virus, and Sendai Virus on Human Lymphocytes and Macrophages, *Infect Immun,* vol. 35; pp. 1142–1146 (1982).

A. Prujansky–Jakobovits et al, Alteration of Lumphocyte Surface Properties by Insertion of Foreign Functional Components of Plasma Membrane, *Proc Natl Acad Sci USA,* vol. 77; pp. 7247–7251 (1980).

K. Leung et al, Selective Suppression of the Cytotoxic T Cell Response to Influenza Virus in Mice, *Eur. J. Immunol,* vol. 10; pp. 803–810 (1980).

K. Megyeri et al, Stimulation of Interferon and Cytokine Gene Expression by Imiquimod and Stimulation by Sendai Virus Utilize Similar Signal Transduction Pathways, *Mol Cell Biol,* vol. 15; pp. 2207–2218 (1995).

S. Hou, Divergence Between Cytotoxic Effector Function and Tumor Necrosis Factor Alpha Production for Inflammatory CD4+ T Cells from Mice with Sendai Virus Pneumonia, *J. Virol.,* vol. 67; pp. 6299–6302 (1993).

M. D'Addario et al, Coordinate Enhancement of Cytokine Gene Expression in Human Immunodeficiency Virus Type 1–Infected Promonocytic Cells, *J. Virol.,* vol. 64; pp. 6080–6089 (1990).

S. Sueishi et al, Effectos of Cytokines from Virus–Induced Human Lymphoblasts on the Growth and Viability of the Promyelocytic Leukemia Cell Line HL–60, *J Interferon Res,* vol. 10; pp. 379–383 (1990).

A. Ray et al, Activation of the Human Beta 2–Interferon/Hepatocyte–Stimulating Factor/Interleukin 6" Promoter by Cytokines, Viruses, and Second Messenger Agonists, *Proc Natl Acad Sci USA,* vol. 85; pp. 6701–6705 (1988).

A.P Bollon et al, Human Cytokines, Tumor Necrosis Factor, and Interferons: Gene Cloning, Animal Studies, and Clinical Trials, *J. Cell Biochem,* vol. 36; pp. 353–367 (1988).

M.A. Wabuke–Bunoti et al, Stimulation of anti–Influenza Cytolytic T Lymphocytes by a Synthetic Peptide of the Influenza Hemagglutinin can be Modulated by at Least Three Independent Helper Factors, *J. Immunol,* vol. 133; pp. 2186–2193 (1984).

R.D. Garman et al, Chromatographic Separation from Known Cytokines of a Helper Factor Necessary for the Generation of Murine Cytolytic T Lymphocytes, *J. Immunol,* vol. 132; pp. 1879–1887 (1984).

E. Dehlin et al, Repression of Beta Interferon Gene Expression in Virus–Infected Cells is Correlated with a Poly(A) Tail Elongation, *Mol Cell Biol,* vol. 16; pp. 468–474 (1996).

G. Aboagye–Matheisen et al, Production of Interferons in Human Placental Trophoblast Subpopulations and Their Possible Roles in Pregnancy, *Clin. Diagn. Lab. Immunol.,* vol. 1; pp. 650–659 (1994).

N. Dejucq et al, Interferon–Alpha and –Gamma Expression in the Rat Testis, *Endocrinology,* vol. 136; pp. 4925–4931 (1995).

M. Dipaola et al, Interferon–Alpha 2 Produced by Normal Human Leukocytes is Predominantly Interferon–Alpha 2b, *J Interferon Res,* vol. 14; pp. 325–332 (1994).

X.Y. Mo et al, Induction of Cytokines in Mice with Parainfluenza Pneumonia, *J. Virol,* vol. 69; pp. 1288–1291 (1995).

P. King et al, The Beta–Interferon Promoter Responds to Priming Through Multiple Independent Regulatory Elements, *J. Biol Chem,* vol. 269; pp. 30609–30615 (1994).

M.J. Ellis et al, NF–Kappa B–Independent Activation of Beta–Interferon Expression in Mouse F9 Embryonal Carcinoma Cells, *Nucleic Acids Res,* vol. 22; pp. 4489–4496 (1994).

D. M. Katschinski et al, Influence of Various Factors on Interferon–Alpha Production in Cultures of Human Leukocytes, *J. Interferon Res,* vol. 14; pp. 105–110 (1994).

S.B. Feldman et al, Viral Induction of Low Frequency Interferon–Alpha Producing Cells, *Virology,* vol. 204; pp. 1–7 (1994).

T. Mori et al, A High–Level and Regulatable Production System for Recombinant Glycoproteins Using a Human Interferon–Alpha Promoter–Based Expression Vector, *Gene,* vol. 144; pp. 289–293 (1994).

E. Garoufalis, Viral Induction of the Human Beta Interferon Promoter; Modulation of Transcription by NF–Kappa B/Rel Proteins and Interferon Regulatory Factors, *J Virol,* vol. 68; 4707–4715 (1994).

A. Roulston, Virus Induction of NF–Kappy B/Rel Proteins and Type I Interon Gene Expression in Myelomonoblastic Cells, *Leukemia,* vol. 8; pp. S170–S174 (1994).

G. Aboagye–Mathiesen et al, Human Trophoblast Interferons, *Antiviral Res,* vol. 22; pp. 91–105 (1993).

A. Roulston, Chronic Human Immunodeficiency Virus Type 1 Infection Stimulates Distinct NF–Kappa B/Rel DNA Binding Activities in Myelomonoblastic Cells, *J Virol,* vol. 67; pp. 5235–5246 (1993).

I. Rosztoczy et al, Priming Does Not Change Promoter Sequence Requirements for IFN Induction or Correlate with the Expression of IFN Regulatory Factor–1, *J. Immunol,* vol. 151; pp. 1303–1311 (1993).

K.C. Zoon et al, Purification and Characterization of Multiple Components of Human Lymphoblastoid Interon–alpha, vol. *J. Biol Chem,* vol. 267; pp. 15210–15216 (1992).

F.D. Toth et al, Interferon Production by Cultured Human Trophoblasts and Choriocarcinoma Cell Lines Induced by Sendai Virus, *J Gen Virol,* vol. 71 (Pt. 12); pp. 3067–3069 (1990).

S. Sueishi et al, Effects of Cytokines from Virus–Induced Human Lymphoblasts on the Growth and Viability of the Promyelocytic Laukemia Cell Line HL–60, *J Interferon Res,* vol. 10; pp. 379–383 (1990).

K.J. Busam et al, Virus–vs Endotoxin–Induced Activation of Liver Macrophages, *Eur J. Biochem,* vol. 191; pp. 577–582 (1990).

J. Hiscott et al, Induction of Human Interferon Gene Expression is Associated with a Nuclear Factor that Interacts with the NF–Kappa B Site of the Human Immunodeficiency Virus Enhancer, *J Virol,* vol. 63; pp. 2557–2566 (1989).

J. Van Damme et al, Simultaneous Production of Interleukin 6, Interferon–Beta and Colony–Stimulating Activity by Fibroblasts After Viral and Bacterial Infection, *Eur J. Immunol,* vol. 19; pp. 163–168 (1989).

D.G. Brownstein et al, Immunostimulation in Mice Infected with Sendai Virus, *Am J Vet Res,* vol. 48; pp. 1692–1696 (1987).

D. Aderka et al, Tumor Necrosis Factor Induction by Sendai Virus, *J Immunol,* vol. 136; pp. 2938–2942 (1986).

P.J. Neame et al, A Simple Methodology for the Routine Production and Partial Purification of Human Lymphoblastoid Interferon, *Adv Exp Med Biol,* vol. 172; pp. 269–279 (1984).

Y. Ito et al, Component(s) of Sendai Virus that can Induce Interferon in Mouse Spleen Cells, *Infect Immun,* vol. 39; pp. 1019–1023 (1983).

X. Zhou, Characterization of TAP–Independent and Brefeldin A–Resistant Presentation of Sendai Virus Antigen to CD8+Cytotoxic T Lymphocytes, *Scand J Immunol,* vol. 42; pp. 66–75 (1995).

T. Liu et al, Heat–Inactivated Sendai Virus can Enter Multiple MHC Class I Processing Pathways and Generate Cytotoxic T Lymphocyte Responses In Vivo, *J Immunol,* vol. 154; pp. 3147–3155 (1995).

S. Hou et al, Host Response to Sendai Virus in Mice Lacking Class II Major Histocompatibility Complex Glycoproteins, *J Virol,* vol. 69; pp. 1429–1434 (1995).

C. Ewing et al, Virus–Specific CD8+T–Cell Responses in Mice Transgenic for a T–Cell Receptor Beta Chain Selected at Random, *J. Virol,* vol. 68; pp. 3065–3070 (1994).

X. Zhou et al, Antigen Processing Mutant T2 Cells present Viral Antigen Restricted Through H–2Kb, *Eur J Immunol,* vol. 23; pp. 1802–1808 (1993).

X. Zhou et al, TAP2–Defective RMA–S Cells Present Sendai Virus Antigen to Cytotoxic T Lymphocytes, *Eur J Immunol,* vol. 23; pp. 1796–1801 (1993).

S. Hou et al, Delayed Clearance of Sendai Virus in Mice Lacking Class I MHC–Restricted CD8+T Cells, *J Immunol,* vol. 149; pp. 1319–1325 (1992).

A. Taku et al, A Helper Factor Needed for the Generation of Mouse Cytolytic T Lymphocytes is Made by Tumor Cell Lines, Cloned T Cells, and Spleen Cells Exposed to a Variety of Stimuli, *J Immunol,* vol. 133; pp. 502–508 (1984).

D.T. Harris et al, Antigen Recognition by H–2–Restricted Cytolytic T Lymphocytes is not Mediated by Two Independent Receptors, *J Exp Med,* vol. 159; pp. 330–335 (1984).

D.T. Harris et al, Direct Transfer of Antigen–Specific Cytolytic Activity to Noncytolytic Cells Upon Fusion with Liposomes Derived from Cytolytic T Cell Clones, *J Exp Med,* vol. 159; pp. 261–275 (1984).

A.H. Hale et al, Elicitation of Anti–H–2 Cytotoxic T Lymphocytes with Antigen–Modified H–2 Negative Stimulator Cells, *J Immunol,* vol. 126; pp. 1485–1488 (1981).

M. McGee et al, Elicitation of Primary Anti–Sendai Virus Cytotoxic T Lymphocytes with Purified Viral Glycoproteins, *Eur J Immunol,* vol. 10; pp. 923–928 (1980).

A.H. Hale et al, Antigen–Liposome Modification of Target Cells as a Method to Alter Their Susceptibility to Lysis by Cytotoxic T Lymphocytes, *Proc Natl Acad Sci USA,* vol. 77; pp 6105–6108 (1980).

A.H. Hale et al, Elicitation of Anti–Viral Cytotoxic T Lymphocytes with Purified Viral and H–2 Antigens, *J Immunol,* vol. 125; pp. 428–430 (1980).

U.H. Kaszinowski, Recognition of Viral Glycoproteins by Influenza A–Specific Cross–Reactive Cytolytic T Lymphocytes, *J Exp Med,* vol. 151; pp. 945–958 (1980).

A.H. Hale et al, Minimal Molecular Requirements for Reactivity of Tumor Cells with T Cells, *J Immunol,* vol. 124; pp. 2063–2070 (1980).

Y. Fukami et al, Difference in Capacity of Sendai Virus Envelope Components to Induce Cytotoxic T Lymphocytes in Primary and Secondary Immune Responses, *Infect Immun,* vol. 26; pp. 815–821 (1979).

A.H. Hale et al, Elicitation of Anti–Sendai Virus Cytotoxic T Lymphocytes by Viral and H–2 Antigens Incorporated into the Same Lipid Bilayer by Membrane Fusion and by Reconstitution into Lyposomes, *J Immunol,* vol. 124; pp. 724–732 (1980).

R. Finberg et al, The Induction of Virus–Specific Cytotoxic T Lymphocytes with Solubilized Viral and Membrane Proteins, *J Exp Med,* vol. 148; pp. 1620–1627 (1978).

J. Cohen, "Bumps on the Vaccine Road", *Science,* vol. 265, Sep. 2, 1994, pp. 1371–1373.

J. Cohen, "Are Researchers Racing Toward Success, Or Crawling?", *Science,* vol. 265, Sep. 2, 1994, pp. 1373–1375.

R. Nowak, "U.S. National Program is Going Nowhere Fast", *Science,* vol. 265, Sep. 2, 1994, pp. 1375–1376.

A. Gibbons, "Childrens' Vaccine Initiative Stumbles", *Science,* vol. 265, Sep. 2, 1994, pp. 1376–1377.

B.R. Bloom, "The United States Needs a National Vaccine Authority", *Science,* vol. 265, Sep. 2, 1994, pp. 1378–1380.

R.S. Nussenzweig & C.A. Long, "Malaria Vaccines: Multiple Targets", *Science,* vol. 265, Sep. 2, 1994, pp. 1381–1383.

S.A. Plotkin, "Vaccines for Varicella–Zoster Virus and Cytomegalovirus: Recent Progress", *Science,* vol. 265, Sep. 2, 1994, pp. 1383–1385.

G.R. Siber, "Pneumococcal Disease; Prospects for a New Generation of Vaccines", *Science,* vol. 265, Sep. 2, 1994, pp. 1385–1387.

J.J. Mekalanos & J.C. Sadoff, "Cholera Vaccines: Fighting an Ancient Scourge", *Science,* vol. 265, Sep. 2, 1994, pp. 1387–1389.

R.I. Glass et al, "Rotavirus Vaccines: Success by Reassortment?", *Science,* vol. 265, Sep. 2, 1994, pp. 1389–1391.

S. L. Katz et al, Measles Vaccine: Do We Need New Vaccines or New Programs?, *Science,* vol. 265, Sep. 2, 1994, pp. 1391–1392.

C.B. Hall, "Prospects for a Respiratory Syncytial Virus Vaccine", *Science,* vol. 265, Sep. 2, 1994, pp. 1393–1394.

J. Sprent et al, Lymphocyte Life–Span and Memory, *Science,* vol. 265, Sep. 2, 1994, pp. 1395–1400.

N.R. Rabinovich et al, "Vaccine Technologies: View to the Future", *Science,* vol. 265, Sep. 2, 1994, pp. 1401–1404.

Krowka, *J. Immunol.,* 144, #7, pp. 252–255,, Apr. 1990.

Wassely, *Immunol Method,,* 4, p. 217, 1994.

PROTEIN-LIPID VESICLES AND AUTOGENOUS VACCINE COMPRISING THE SAME

This application is a continuation of Ser. No. 08/712,020 filed Sep. 11, 1996 now U.S. Pat. No. 5,834,015.

This invention was made with government support. The government has certain rights in the invention.

FIELD OF THE INVENTION

The present invention relates to novel compositions of matter useful for autogenous vaccines. In one embodiment, the autogenous vaccine is useful to treat individuals infected with human immunodeficiency virus (HIV).

BACKGROUND OF THE INVENTION

This background section synthesizes the most relevant publications and knowledge in the field as seen by one of the inventors (RJM) after successful completion of the invention. Many of the observations and statements are made with the benefit of hindsight. Thus, none of the statements made in the background section is to be construed as representative of the knowledge of those ordinarily skilled in the art as of the filing date.

There are a number of biological characteristics of HIV and its interaction with host defense mechanisms that have so far frustrated the development of effective therapies, including both protective and therapeutic vaccines. Infection with HIV results in multiorgan, intracellular infection that has both a cytolytic and latent stage. There has been a limited number of effective antiretroviral drugs developed to date and these have been associated with the eventual and sometimes rapid development of drug resistance with subsequent clinical deterioration. While there is need to pursue new primary drug therapy of HIV, immune-based therapy, both passive and active, has been recognized as a potential approach to the HIV-infected individual.

It has been felt that an effective HIV vaccine or immunotherapeutic will need to induce a specific and protective cytotoxic T lymphocyte (CTL) response as well as a neutralizing antibody response. Recent studies on the rapid turnover of plasma HIV virions as well as CD4 lymphocytes in HIV-infected individuals have demonstrated that while a low CD4 count corresponds to disease progression, even at markedly depressed CD4 counts, the immune system maintains the ability to mount an effective immune response. Therefore, the HIV-infected individual with advanced AIDS could still have an immune system capable of recognizing and responding to antigenic structures in an appropriately formulated therapeutic vaccine.

Although there is a strong humoral and cellular immune response to primary infection by HIV, in general, this response does not result in long term protection from clinical disease progression, including Acquired Immunodeficiency Syndrome (AIDS). For example, the antigenic variation in the HIV envelope protein has made the development of effective glycoprotein vaccines problematic. Vaccine induced antibody may not be protective against homologous or heterologous strains of HIV. Thus, the success of active therapeutic and prophylactic vaccines or immunotherapies may depend on the ability of the host immune system to recognize and respond to HIV-related and associated antigens in new ways.

One strategy to the preparation of therapeutic vaccines and immunotherapies has been to remove antigenic material (plasma, blood cells, or tissue) from a given patient and process (formulate) the material ex vivo with an adjuvant or immunomodulating agent. These reformulated, patient-specific antigen preparations are then administered to the patient. The goal is to attempt to increase or redirect the immune response to specific antigenic regions, or even to entice the immune system to respond to potentially protective but "hidden", (sequestered) antigens. In addition, the types or balance of the immune responses induced could be altered in a way that results in better clinical outcomes. Such changes would include but are not limited to: humoral versus cell mediated responses, classes of antibody subtypes, T helper cell subsets, activation of T cytotoxic and natural killer cells, and secretion of soluble molecules involved in regulating immune responses, including cytokines and chemokines. This type of formulation has been termed an autogenous vaccine.

The use of autogenous vaccines (AV) has been limited to a few bacteria and several viral-tumor models. For example, the possibility that the immune system is capable of mounting an effective immune response against tumors under certain conditions has been suspected for almost 100 years. This notion is based primarily on the rare but documented phenomenon of spontaneous regression of tumors. However, this notion is also supported by data from in vitro systems that have identified a wide variety of tumor-specific antigens as well as by the development of animal models in which immunization against such antigens resulted in rejection of the tumor cells. In addition, there have been many attempts to utilize immune modulators as therapy for tumors but these have resulted in only a small number of successes. Since human tumors tend to be poorly immunogenic, continued efforts have been made to find substances that can enhance the immune response to tumors.

For more than 60 years, it has been known that on occasion tumors regressed following naturally occurring viral infections. This phenomenon has been called "viral oncolysis." Enveloped viruses including influenza virus, vaccinia virus, and Newcastle disease virus have all been used to induce human tumor regression. Recently, it has been shown, using a model tumor antigen system, that immunizations with recombinant vaccinia virus or recombinant fowlpox virus can stimulate a CTL response sufficient to produce reductions in tumor burden in vivo.

One of the inventors (JMO) has successfully demonstrated the use of AV therapy for the treatment of the papilloma virus induced disease of recurrent juvenile laryngeal papillomata. Over the last 24 years, twenty-eight children with severe recurrent juvenile papilloma of the larynx have been treated with AV's. In these patients, none has had a worsening of tumor growth while 20 (71%) have had a marked reduction or clearing of their tumors.

SUMMARY OF THE INVENTION

Accordingly, one object of the present invention is to provide a composition useful as an autogenous vaccine, especially for treating chronic diseases.

This and other objects have been achieved by providing a protein-lipid vesicle comprising:

A. patient-specific antigen;

B. adjuvant or immunomodulator; and

C. lipid carrier.

The present invention further provides an autogenous vaccine comprising:

A. the protein-lipid vesicle described above; and

B. a pharmaceutically acceptable carrier.

The present invention also provides a method for treating chronic diseases comprising administering to a patient in need of treatment an effective amount of an autogenous vaccine comprising the above-described protein-lipid vesicle.

In a preferred embodiment, the protein-lipid vesicle comprises patient-specific antigens from individuals infected with HIV and the vaccine is useful in treating such individuals.

DETAILED DESCRIPTION OF THE INVENTION

Structure of Protein-Lipid Vesicles

The basic structure of the protein-lipid vesicles is a liposome as previously described by, for example, Gould-Fogerite, et al., ("The Reconstitution of Biologically Active Glycoproteins into Large Liposomes: Use As A Delivery Vehicle to Animal Cells," *Advances in Membrane Biochemistry and Bioenergetics*, C. Kim, et al, Editors. (Plenum Publishing Corp., 1988)) and references 1 to 24 cited therein; and Papahadjopoulos (U.S. Pat. No. 4,078,052, which is incorporated herein by reference); or a proteoliposome as previously described by Mannino, et al. (U.S. Pat. Nos. 4,663,161 and 4,871,488, both of which are expressly incorporated herein by reference).

The protein-lipid vesicles according to the present invention comprise patient-specific antigen; adjuvant or immunomodulator; and lipid carrier. Preferably they also comprise negatively charged lipid, in addition to the lipid carrier.

The patient-specific antigens are obtained from plasma, cells, or tissue specimens.

The cells are pelleted and then extracted with detergent in a physiologically balanced buffer, except that the buffer has a salt concentration from about 1 to about 6 M. Preferably the detergent is a nonionic detergent such as $\beta$,D-octylglucoside, and preferably the salt concentration is about 2 M.

Similarly, tissue is disrupted by known physical techniques, such as grinding in a Dounce homogenizer, or by known chemical techniques, such as treatment with appropriate enzymes (collagenase or trypsin), and then extracted with detergent in an appropriate physiologically balanced buffer, but having a salt concentration of from about 1 to about 6 M as described above.

As described in more detail below, the adjuvant or immunomodulator can comprise envelope proteins derived from human or animal viruses or can be chemical in nature.

The adjuvant/immunomodulator needs to maintain its physiological activity in the protein-lipid vesicle. That is, the adjuvant/immunomodulator must at least maintain its ability to induce changes in the immune response. Thus, if the adjuvant/immunomodulator is envelope protein derived from animal viruses, the envelope protein needs to be extracted with appropriate extraction buffer such as that described above for extracting the patient-specific antigens.

As the lipid carrier, any lipid can be used. Desirably, the lipids comprising the carrier are not immunogenic. Examples of suitable lipids include phospholipids such as phosphatidylserine and phosphatidylethanolamine; sterols such as cholesterol; sphingolipids such as sphingomyelin; and glycolipids such as myelin. Phospholipids, sphingolipids or sterols that are components of membranes of eukaryotic or prokaryotic cells are useful.

In a preferred embodiment, the protein-lipid vesicle additionally comprises a negatively charged lipid, more preferably a phospholipid, and most preferably phosphatidylserine (PS).

This is in contrast to phosphatidylcholine which is used in traditional liposome preparations. PS-based preparations appear to serve as stronger adjuvants in the absence of toxic side effects. One potential explanation for these observations is that lipid vesicles with a predominance of negatively charged lipid (especially phosphatidylserine) on their outside surface are efficiently scavenged by antigen-processing cells. These scavenger cells have been shown to have phosphatidylserine-specific receptors on their surfaces.

The relative amounts of the components of the protein-lipid vesicles can be determined by one of ordinary skill in the art based on the source of the patient-specific antigen, the character of the adjuvant/immunomodulator, the presence or absence of negatively charged lipid, the method of making the vesicles and the pharmaceutically acceptable carrier that will be used in the vaccine formulation.

The AV used in the working examples comprises about 0.47 mg Sendai envelope proteins, about 0.47 mg Sendai envelope lipids, about 1.68 mg phosphatidylserine, and about 0.187 mg cholesterol. This formulation is delivered with about 1 ml of patient plasma.

Patient-Specific Antigen

According to the present invention, the patient-specific antigens are those produced in chronic diseases including chronic viral diseases, cancers and parasitic diseases.

Examples of chronic viral diseases include, but are not limited to, disease from infection with human immunodeficiency viruses, papilloma viruses, and herpes viruses.

Examples of specific cancers include, but are not limited to, sarcomas, lymphomas, adenomas, neuromas, carcinomas, myelomas, melanomas, leukemias, and endotheliomas.

Parasitic chronic diseases refer to infections with animal parasites including, but not limited to protozoa, helminths and ectoparasites. Specific examples include, but are not limited to, malaria, plasmodia, nematodes, toxoplasma, trypanosoma, schistosoma, nippostrongylus, ascaris, leishmania, entamoeba, and trichinella.

The patient-specific antigens can be derived from a variety of cells, tissues, and organs in a given individual. Those of ordinary skill in the art could readily determine what cells, tissues, or organs would express the patient-specific antigen.

For example, patient-specific antigens from individuals infected with HIV can be derived from mononuclear cells found in the blood, as described in more detail below. Other sources of the patient-specific antigen from individuals infected with HIV include lymph nodes, bone marrow, and plasma.

Similarly, lymphocytes are sources of patient-specific antigens for treating lymphomas; a biopsy of tumor tissue from the lung is a suitable source of patient-specific antigen for treatment of small cell carcinoma of the lung; a biopsy of one of the papillomas is a source of patient-specific antigen for treatment of various papillomas; and cells infected with the malaria parasite, such as red blood cells and hepatocytes, are sources of patient-specific antigen for treatment of malaria.

Choice of Adjuvant/Immunomodulator Agent

The autogenous vaccine of the present invention is based on two premises: (i) the use of antigens currently present in the patient at a specific point in the course of the disease, and (ii) re-exposure of these antigens to the immune system in a new and more stimulatory way, especially through the inclusion of adjuvants and immunomodulators.

The use of adjuvants/immunomodulators with such reformulated antigens provides an enhanced ability to stimulate multiple cellular and humoral immune responses. However, the complexity of the immune system, and the numerous factors involved in the stimulation of specific immune responses, indicates that the selection of an appropriate immunomodulator can be important in the formulation of an effective autogenous vaccine preparation.

According to the present invention, suitable adjuvants/immunomodulators include envelope proteins from human or animal viruses as well as specific chemical immunomodulators.

Specific chemical immunomodulators include cytokines, chemokines and lymphokines, including, but not limited to, interferon alpha, interferon gamma, and interleukin 12.

Examples of suitable animal viruses as a source of envelope protein include, but are not limited to, viruses from the following families: Arenaviridae, Bunyaviridae, Coronaviridae, Deltaviridae, Flaviviridae, Herpesviridae, Rhabdoviridae, Retroviridae, Poxviridae, Paramyxoviridae, Orthomyxoviridae, and Togaviridae. Envelope proteins from Paramyxoviridae and Orthomyxoviridae are preferred. Envelope proteins from influenza virus, Newcastle disease virus, and vaccinia virus are preferred. Envelope proteins from Sendai virus are especially preferred.

In the examples below, the envelope glycoproteins and lipids from mouse parainfluenza type 1 virus, i.e., Sendai virus, are used as an adjuvant/immunomodulator to enhance the immune response to an autogenous HIV/cellular vaccine. This adjuvant has several advantages over Freund's or alum adjuvants by its ability to stimulate humoral immune responses including the induction of broad lgG subclass responses as well as stimulation of CD8 cell mediated CTL responses. In addition, Sendai-derived envelope glycoprotein and lipid (SDE) is a potent stimulator of interferon alpha secretion by human peripheral blood mononuclear cells. Recent evidence suggests that interferon alpha can play a crucial role in regulating immune responses and may favor induction of cell mediated immunity. Most enveloped viruses stimulate only natural interferon producing cells (dendritic type cells) to secrete interferon alpha. In contrast to other viruses and viral envelope derived lipid systems tested, SDE appears to stimulate monocytes and dendritic cells. This could be of significant advantage in AIDS patients who are likely to have decreased dendritic cell populations.

The use of SDE has been shown to be safe in multiple animal studies involving mice, rabbits, guinea pigs and monkeys. As part of an NIH-sponsored comparative adjuvant trial, SDE was administered to eight Rhesus monkeys with formalin fixed Simian Immunodeficiency virus (SIV) four times over a one-and-a half year period. All animals were monitored for reactions at the site of the injection, general clinical, blood chemical or hematological changes, and development of uveitis. In contrast to many of the other adjuvants tested, no undesirable sequelae were detected following administration of SIV formulated with SDE.

The envelope proteins of Sendai virus have been shown to be highly immunopotentiating in a number of studies. For example, it was found that when small amounts of Sendai envelope proteins were integrated into a lipid matrix containing a synthetic peptide, antibody responses to normally poorly immunogenic B cell determinants were induced.

CD8+ cells play an important role in the development of effective CTL responses. In previous studies, the integration of SDE into a lipid matrix was shown to be a highly effective adjuvant in a primate AIDS model, generating SIV-specific strong T-cell help and cytotoxic T-cell responses, and low levels of neutralizing antibodies (unpublished observations). In a separate study, a peptide representing a cytotoxic T-cell epitope from SIV was formulated with SDE and injected intramuscularly into Rhesus monkeys. Strong SIV-specific cytotoxic T-cell responses were detected after a single injection. These responses lasted many months and were boosted on subsequent immunization. Consistent with all studies to date, no negative local or systemic side effects were detected.

In other studies in mice, SDE has been shown to adjuvant antibody and cellular immune responses to HIV-derived proteins and peptides. Also, when peptides from the human immunodeficiency virus (HIV) envelope glycoprotein formulated into a proteoliposome with the Sendai-lipid material were injected into BALB/c mice, a CTL response to HIV gp160 was observed. Furthermore, the activation of CTL occurred even when CD4+ cells were depleted. Recently, it was also shown that in mice, the generation of specific CTL to Sendai antigen did not require CD4+ cells. This observation has significant implications for the treatment of the CD4-deficient immunologically compromised AIDS patients.

In summary, SDE has been shown to be a safe and effective adjuvant/immunomodulator for a variety of antigens including those derived from human immunodeficiency viruses.

The autogenous vaccine of the present invention comprises the above-described protein-lipid vesicle and a pharmaceutically acceptable carrier, diluent or excipient.

Examples of suitable pharmaceutically acceptable carriers, diluents and/or excipients include the patient's serum or plasma, balanced saline solutions, any aqueous buffer, water and any of numerous inert carriers. The patients' serum or plasma is especially preferred.

The dosage form can be oral, nasal, intramuscular, intravenous, intraperitoneal, intraocular, subcutaneous, intradermal, or on any mucosal surface.

Although the dosage varies with the nature of the chronic disease for which treatment is sought, one skilled in the art can readily determine suitable dosages.

In addition, repeated immunizations at appropriately spaced intervals are preferred. The intervals are spaced so that the effect of the latter immunization can build on that of the former immunization. In the preferred treatment regime, immunizations would not be repeated over less than 4-week intervals. However, the intervals could extend for years depending upon the disease/condition being treated. One of ordinary skill in the art can devise appropriate dosage regimes based upon experiences with other AV vaccines and the standard primary regimes used for cellular/killed vaccines.

EXAMPLES

The present invention will now be described by reference to the following working examples, which are not meant to be limiting.

Outline of Clinical Study

Due to the lack of an adequate animal model for the study of HIV infection in vivo or for the evaluation of response to new potential therapies, the following phase I/II study in humans for the use of an autogenous HIV cellular vaccine was initiated. Such a study in HIV-infected individuals was warranted by the progressive eventual fatal course of HIV infection, the lack of long term effective drug therapies and the disappointment with present HIV subunit vaccine trials. This study was designed to determine whether an AV prepared sequentially from the peripheral blood of an HIV-infected individual, including both cell associated antigens and free virus, will induce a safe and effective immune response to autologous virus and disrupted virus associated cell surface proteins. In order to enhance the immune response to this whole autogenous HIV/cellular vaccine, it was combined with SDE. The sequential preparation of four autogenous vaccines during a proposed 32-week primary immunizing period allowed for a more specific immune response should there be a change or drift in the circulating viral strains of the patient during the course of this proposed active therapeutic immune trial.

Patients were recruited into this study 4 to 8 weeks prior to the first planned dose of the autogenous vaccine so that an autogenous B-cell line could be established for future cytotoxic T-lymphocyte assays. Baseline pre-vaccine laboratory studies were performed on day −1 when blood was also taken for AV #1 preparation and day 0 immediately before the first vaccine dose is given. Patients were given 1 ml of the vaccine intramuscularly (IM) into both anterior-lateral thighs. Six weeks after dose AV #1, 10 ml of blood was drawn for the preparation of the next autogenous vaccine (AV #2), to be given within 24 hours after preparation. Six weeks after the dose of AV #2 (study week #12) 10 ml of blood was drawn from the patient for the preparation of the third autogenous vaccine (AV #3) to be given within 24 hours after preparation. Patients next had blood drawn for the preparation of the fourth autogenous vaccine (AV #4), at study week #24. The regime for the autogenous HIV/cellular vaccine was based on past experiences with other AV's and the standard primary regime used for cellular/killed vaccines.

Subjects

The more rapid progression of HIV infection in children argued that both adults and perinatally infected children (>15 months of age) should be included in this phase I/II vaccine trial. Both adults/adolescents and children >15 months were enrolled concurrently. Initially five HIV-infected adults/adolescents and five HIV-infected children were selected for autogenous HIV/cellular vaccine therapy. All selected patients had developed clinical symptomatic disease. Patients were considered infected if they had a positive HIV ELISA confirmed by Western blot on two occasions after 18 months of age or had a combination of two positive HIV specific tests (HIV culture, HIV DNA PCR, or HIV P-24 Ag). Patients with only AIDS defining illness without the above confirmatory laboratory studies were not enrolled.

Preparation of Autogenous HIV/Cellular Vaccine

The preparation of the sequential autogenous HIV/cellular vaccine with the addition of the SDE adjuvant is detailed below.

Ten ml of blood was drawn in acid citrate-dextrose (ACD—yellow top) vacutainer tubes. Plasma was harvested and saved. Mononuclear cells (MNC) were separated from red blood cells (RBC) and polymorphonuclear leukocytes (PML) by Ficoll Hypaque gradient centrifugation. The isolated MNC were washed ×3 in Hank's balanced salt solution without calcium and magnesium. Following the third wash, the supernatant was removed and discarded.

SDE was prepared as previously described (Mannino, et al. U.S. Pat. Nos. 4,663,161 and 4,871,488). Sendai virus was thawed, transferred to sterile thick-walled polycarbonate tubes, and diluted with TES buffer (2 mM TES, 2 mM L-histidine, 100 mM NaCl (pH 7.4)). The suspension was centrifuged at 60,000×g for 50 minutes at 4° C. The supernatant was removed and the pellet was resuspended by vortexing and sonicating to a concentration of 2 mg viral protein/ml of extraction buffer (2 M NaCl, 0.02 M sodium phosphate buffer (pH 7.4)). The nonionic detergent β-D-octyl-glucopyranoside (OCG) was added to a concentration of 2% w/v. The suspension was vortexed, sonicated for 5 seconds, placed in a 37° C. waterbath for 45 minutes (sonicated for 5 seconds every fifteen minutes), and centrifuged at 60,000×g for 50 minutes. The supernatant was removed and used in the formation of protein-lipid autogenous vaccine formulations containing lipid bilayer-integrated viral and cellular proteins.

The envelope glycoproteins of Sendai virus account for about 33% of the total viral protein and are present in approximately equal weight to the viral lipid. An amount of phosphatidylserine (PS) and cholesterol (CH) (9:1 wt. ratio) equal to four times the weight of the Sendai viral lipid that was extracted, was dried under nitrogen in a clean glass tube. Supernatant from the OCG-extracted virus preparation was added to the dried lipid and the solution was vortexed for 7 minutes. The solution was incubated on ice for 1 hour and passed through a 0.2 μm filter.

An aliquot of this solution (712 μl) containing approximately 0.47 mg Sendai glycoproteins, 0.47 mg viral envelope lipid, with 1.68 mg synthetic phosphatidylserine (1,2 dioleoyl-sn-Glycero-3-[Phospho-L-Serine]-sodium salt,) and 0.187 mg cholesterol (Avanti Polar Lipids) as carrier, was added to the cell pellet (final volume about 1 ml). The sample was sonicated for 10 seconds and incubated at room temperature for 10 minutes followed by incubation at 37° C. for 20 minutes. Detergent was removed by dialysis against four changes (100 ml overnight, then 250 mls, 3 changes at 2 hr. intervals) of sterile TES buffer (100 mM NaCl, 2 mM histidine, 2 mM TES, pH 7.4).

The sample (approximately 1 ml) was removed from the dialysis bag and 1 ml of the saved autogenous plasma was added. The vaccine was administered by IM injections in the anterior-lateral thigh of both legs to maximize exposure to the lymphatic system. The autogenous HIV/cellular antigens and the SDE adjuvant were produced as closely as possible to good manufacturing processing conditions, including dedicated materials, hood space, chemicals, and the use of water for irrigation for buffer preparations. Sterile conditions were maintained throughout handling and preparation.

SDE consists only of the envelope glycoproteins and lipids of mouse parainfluenza virus type 1. The high salt and detergent extraction and physical separation from the nucleocapsids, as well as the presence of RNAses, destroys infectious potential as has been shown in an extremely sensitive culture system. It is extremely likely these conditions also inactivated any HIV present in the cells of the patient sample.

The AV was prepared from at least 10 million MNC's for cell associated virus and cell associated cellular proteins. The autologous plasma was used as a vehicle for the vaccine cell material and might have contained cell free virus particles.

Results

1. Patient Characteristics

Eight patients were enrolled and six have completed the initial primary four dose series (with two of those receiving a fifth booster dose). Two were given two doses, with the last receiving three doses of the AV. Four of the patients were under 10 years of age, three were youths 10–16 years of age, and one was a 32-year old adult. Six patients acquired HIV by perinatal exposure, one from a blood transfusion, and the adult patient from sexual exposure. Patients ranged in CDC classification from B1 to C3. There were three females and five males.

2. Safety Data

Over 20 months with the preparation and administration of 28 doses to eight patients, there were no adverse effects and no patients were discontinued from study participation due to local or systemic toxicities. Except for brief local discomfort at the injection site, there were no adverse reactions to the AV. There were no changes of vital signs or acute allergic reactions or delayed local or systemic reactions to the administration of this AV.

Laboratory studies for adverse events including evaluation for hematological safety (CBC, platelet count), autoimmune reaction (ANA), and organ toxicities (multiple blood chemistries) have not shown any significant changes from baseline studies.

3. Efficacy Data

Initial evaluation of possible HIV efficacy included subjective and objective clinical evaluations of disease state and laboratory parameters, including changes in lymphocyte subsets (total lymphocytes, CD3, CD4, and CD8 counts) and HIV plasma viral load by RNA PCR. All eight patients showed no progression of disease, remaining in their initial CDC classification during the course of the AV trial. All patients/guardians reported subjective improvement with AV therapy, including overall improvement in quality of life.

Further, some interesting and encouraging trends are emerging. There was a reversal in the downward trend of CD4 counts and stabilization in all five subsets, with marked increase in three patients. All patients showed a stabilization or an increase in total lymphocyte counts. The expected increase in CD8 cells seen with HIV disease progression did not occur in the AV-treated patients. During AV therapy, two patients demonstrated a decrease in HIV plasma viral load, as evidenced by RNA plasma viral studies, and the remaining patients had fairly stable viral loads.

The clinical and laboratory studies of the recipients of the AV of the invention are suggestive evidence that this immune-based therapy has resulted in:

1. no demonstration of any clinical acute or delayed adverse effects or toxicities;

2. no laboratory evidence of acute or delayed evidence of hematological or organ toxicities;

3. clinical evidence of HIV disease stabilization and improvement in quality of life; and 4. laboratory evidence of AV efficacy with stabilization/improvement in immune status and stabilization/decrease in viral load.

4. Conclusion

The magnitude of the efficacy of this AV immune-based therapy has undergone preliminary statistical analysis based on comparison with natural history data that shows a progressive decrease in CD4 counts over time and a corresponding increase in viral load. The preliminary data analysis encouraged the decision to continue enrollment of patients into this study and to further develop this concept for the use of this novel immune-based treatment for HIV-infected patients. This concept may lead to the future development of a prophylactic vaccine based on the experience gained from the therapeutic HIV vaccine.

While the invention has been described in detail, and with reference to specific embodiments thereof, it will be apparent to one skilled in the art that various changes and modifications can be made therein without departing from the spirit and the scope thereof.

What is claimed is:

1. A protein-lipid vesicle comprising:

A. autogenous, patient-specific antigen from a patient that has a chronic infectious disease wherein the antigen is obtained from the group consisting of plasma, blood cells, tissue and organs, and is prepared by extraction with nonionic detergent in physiologically balanced buffer, but having a salt concentration of from about 1 to about 6 M;

B. an immunomodulator selected from the group consisting of a viral envelope protein and a chemical involved in regulating immune responses; and C. a lipid vesicle further comprising a nonimmunogenic lipid selected from the group consisting of a phospholipid, a sphingolipid, and a sterol.

2. A protein-lipid vesicle comprising:

A. autogenous, patient-specific antigen from a patient that has a chronic infectious disease wherein the antigen is obtained from the group consisting of plasma, blood cells, tissue and organs, and is prepared by extraction with nonionic detergent in physiologically balanced buffer, but having a salt concentration of from about 1 to about 6 M;

B. an immunomodulator selected from the group consisting of a viral envelope protein and a chemical involved in regulating immune responses; and C. a lipid vesicle further comprising a nonimmunogenic lipid selected from the group consisting of a phospholipid, a sphingolipid, and a sterol, and further wherein said lipid is a negatively charged lipid.

3. The protein-lipid vesicle of claim 2, wherein the negatively charged lipid is phosphatidylserine.

4. The protein-lipid vesicle of claim 2, wherein the negatively charged lipid is a phospholipid.

5. The protein-lipid vesicle of claim 1 or 2, wherein the chronic infectious disease is a chronic viral disease.

6. The protein-lipid vesicle of claim 1 or 2, wherein the chronic infectious disease is a chronic viral disease selected from the group consisting of disease resulting from infection with human immunodeficiency viruses, disease caused by infection with papilloma viruses and disease caused by infection with herpes viruses.

7. The protein-lipid vesicle of claim 1 or 2, wherein the chronic infectious disease is a disease caused by infection with human immunodeficiency viruses.

8. The protein-lipid vesicle of claim 1 or 2, wherein the chronic infectious disease is a parasitic infectious disease.

9. The protein-lipid vesicle of claim 1 or 2, wherein the chronic infectious disease is a parasitic infectious disease from infection with a parasite selected from the group consisting of protozoa, helminths and ectoparasites.

10. The protein-lipid vesicle of claim 1 or 2, wherein the immunomodulator is an envelope protein of an animal or human virus.

11. The protein-lipid vesicle of claim 10, wherein the immunomodulator is prepared by extraction with nonionic detergent in physiologically balanced buffer, but having a salt concentration of from about 1 to 6 M.

12. The protein-lipid vesicle of claim 1 or 2, wherein the immunomodulator is an envelope protein of an animal virus.

13. The protein-lipid vesicle of claim 12, wherein the immunomodulator is prepared by extraction with nonionic detergent in physiologically balanced buffer, but having a salt concentration of from about 1 to about 6 M.

14. The protein-lipid vesicle of claim 1 or 2, wherein the immunomodulator comprises envelope protein of an animal virus selected from the group consisting of orthomyxo, paramyxo and pox viruses.

15. The protein-lipid vesicle of claim 14, wherein the immunomodulator is prepared by extraction with nonionic detergent in physiologically balanced buffer, but having a salt concentration of from about 1 to about 6 M.

16. The protein-lipid vesicle of claim 1 or 2, wherein the immunomodulator is envelope protein of an animal virus from the family Paramyxoviridae.

17. The protein-lipid vesicle of claim 16, wherein the immunomodulator is prepared by extraction with nonionic detergent in physiologically balanced buffer, but having a salt concentration of from about 1 to about 6 M.

18. The protein-lipid vesicle of claim 1 or 2, wherein the immunomodulator is envelope protein of Sendai virus.

19. The protein-lipid vesicle of claim 18, wherein the immunomodulator is prepared by extraction with nonionic detergent in physiologically balanced buffer, but having a salt concentration of from about 1 to about 6 M.

20. The protein-lipid vesicle of claim 1, wherein the immunomodulator is a chemical involved in regulating immune responses.

21. The protein-lipid vesicle of claim 20, wherein the immunomodulator is a chemical selected from the group consisting of cytokines, chemokines and lymphokines.

22. The protein-lipid vesicle of claim 21, wherein the immunomodulator is a chemical selected from the group consisting of interferon alpha, interferon gamma and interleuken 12.

23. A protein-lipid vesicle comprising:
   A. autogenous, patient-specific antigen from a patient that has neoplasia, wherein the antigen is prepared from tumor tissue by extraction with nonionic detergent in physiologically balanced buffer, but having a salt concentration of from about 1 to about 6M;
   B. an immunomodulator selected from the group consisting of a viral envelope protein and a chemical involved in regulating immune responses; and
   C. a lipid vesicle further comprising a nonimmunogenic lipid selected from the group consisting of a phospholipid, a sphingolipid, and a sterol.

24. A protein-lipid vesicle comprising:
   A. autogenous, patient-specific antigen from a patient that has neoplasia, wherein the antigen is prepared from tumor tissue by extraction with nonionic detergent in physiologically balanced buffer, but having a salt concentration of from about 1 to about 6M;
   B. an immunomodulator selected from the group consisting of a viral envelope protein and a chemical involved in regulating immune responses; and
   C. a lipid vesicle further comprising a nonimmunogenic lipid selected from the group consisting of a phospholipid, a sphingolipid, and a sterol, and further wherein said lipid is a negatively charged lipid.

25. The protein-lipid vesicle of claim 24, wherein the negatively charged lipid is phosphatidylserine.

26. The protein-lipid vesicle of claim 23 or 24, wherein the neoplasia is a sarcoma, lymphoma, adenoma, neuroma, carcinoma, myeloma, melanoma, leukemia, or endothelioma.

27. The protein-lipid vesicle of claim 22 or 24, wherein the immunomodulator is an envelope protein of an animal or human virus, prepared by extraction with nonionic detergent in physiologically balanced buffer, but having a salt concentration of from about 1 to about 6 M.

28. The protein-lipid vesicle of claim 23 or 24, wherein the immunomodulator is an envelope protein of an animal virus, prepared by extraction with nonionic detergent in physiologically balanced buffer, but having a salt concentration of from about 1 to about 6 M.

29. The protein-lipid vesicle of claim 23 or 24, wherein the immunomodulator comprises envelope protein of an animal virus selected from the group consisting of orthomyxo, paramyxo and pox viruses, prepared by extraction with nonionic detergent in physiologically balanced buffer, but having a salt concentration of from about 1 to about 6 M.

30. The protein-lipid vesicle of claim 23 or 24, wherein the immunomodulator is envelope protein of an animal virus from the family Paramyxoviridae, prepared by extraction with nonionic detergent in physiologically balanced buffer, but having a salt concentration of from about 1 to about 6 M.

31. The protein-lipid vesicle of claim 23 or 24, wherein the immunomodulator is envelope protein of Sendai virus, prepared by extraction with nonionic detergent in physiologically balanced buffer, but having a salt concentration of from about 1 to about 6 M.

32. The protein-lipid vesicle of claim 31, wherein the immunomodulator is a chemical selected from the group consisting of cytokines, chemokines and lymphokines.

33. The protein-lipid vesicle of claim 33, wherein the immunomodulator is a chemical selected from the group consisting of interferon alpha, interferon gamma, and interleuken 12.

34. An autogenous vaccine comprising:
   A. the protein-lipid vesicle of claim 1 or 23; and
   B. a pharmaceutically acceptable carrier, diluent or excipient.

35. A method for treating chronic disease comprising administering to a patient in need of treatment an effective amount of the protein-lipid vesicle of claim 1 or 23.

36. The protein-lipid vesicle of claim 1, wherein said immunomodulator is a chemical immunomodulator or derived from viral coat protein.

37. The protein-lipid vesicle of claim 2, wherein said immunomodulator is a chemical immunomodulator or derived from viral coat protein.

38. The protein-lipid vesicle of claim 23, wherein said immunomodulator is a chemical immunomodulator or derived from viral coat protein.

39. The protein-lipid vesicle of claim 24, wherein said immunomodulator is a chemical immunomodulator or derived from viral coat protein.

* * * * *